US010450238B2

(12) United States Patent
Caesar

(10) Patent No.: US 10,450,238 B2
(45) Date of Patent: Oct. 22, 2019

(54) WORM HARVESTING APPARATUS

(71) Applicant: Avraham Caesar, Haifa (IL)

(72) Inventor: Avraham Caesar, Haifa (IL)

(*) Notice: Subject to any disclaimer, the term of this patent is extended or adjusted under 35 U.S.C. 154(b) by 439 days.

(21) Appl. No.: 15/309,186

(22) PCT Filed: May 11, 2015

(86) PCT No.: PCT/IL2015/050490
§ 371 (c)(1),
(2) Date: Nov. 6, 2016

(87) PCT Pub. No.: WO2015/173804
PCT Pub. Date: Nov. 19, 2015

(65) Prior Publication Data
US 2017/0066698 A1  Mar. 9, 2017

(30) Foreign Application Priority Data

May 12, 2014 (IL) .......................................... 232567

(51) Int. Cl.
*A01K 29/00* (2006.01)
*C05F 17/00* (2006.01)
(Continued)

(52) U.S. Cl.
CPC ...... *C05F 17/0009* (2013.01); *A01K 67/0332* (2013.01); *C05F 17/0258* (2013.01); *Y02P 20/145* (2015.11); *Y02W 30/43* (2015.05)

(58) Field of Classification Search
CPC ... C05F 17/00; C05F 17/0247; C05F 17/0009
(Continued)

(56) References Cited

U.S. PATENT DOCUMENTS 3,768,442 A    10/1973  Van Huis
3,961,603 A *   6/1976  Gaddie, Sr. ........ A01K 67/0332
                                                       119/6.7
(Continued)

FOREIGN PATENT DOCUMENTS

CA         2275783 A1    12/2000
CN       101597564       12/2009
(Continued)

*Primary Examiner* — Richard T Price, Jr.
(74) *Attorney, Agent, or Firm* — Mark M. Friedman

(57) ABSTRACT

A vermiculture unit comprises structural elements defining an interior fillable with organic substance and through which worms for converting the organic substance to environmentally compatible products migrate; a perforated surface for supporting the organic substance; and fixed walls extending upwardly from the perforated surface to a void area located below an uppermost edge of the structural elements, removal of worms from the interior that is below the void area being prevented by the fixed walls. An extractor is insertable into the interior via the void area, for extracting from the interior, solidified organic substance to which the worms have upwardly migrated, allowing grown worms to be separated from the extracted organic substance and collected. In one embodiment, the extractor is an openwork drawer member. In another embodiment, the structural elements are used for vermicomposting while an inclined surface receives worm processed byproducts downwardly discharged through the perforated surface.

19 Claims, 5 Drawing Sheets

(51) Int. Cl.
*A01K 67/033* (2006.01)
*C05F 17/02* (2006.01)

(58) Field of Classification Search
USPC .......................................... 119/6.4–6.8, 270
See application file for complete search history.

(56) References Cited

U.S. PATENT DOCUMENTS

| | | | |
|---|---|---|---|
| 4,112,872 A | 9/1978 | Van Huis | |
| 4,552,726 A | 11/1985 | Grappelli et al. | |
| 6,474,259 B1* | 11/2002 | Gaugler | A01K 67/033 |
| | | | 119/6.7 |
| 2003/0059931 A1 | 3/2003 | Gitt | |
| 2011/0139075 A1* | 6/2011 | Shapiro Ilan | A01K 67/033 |
| | | | 119/6.5 |
| 2012/0214223 A1* | 8/2012 | Hughes | A01K 67/0332 |
| | | | 435/287.1 |
| 2015/0223496 A1* | 8/2015 | Kitazumi | B09B 5/00 |
| | | | 119/6.5 |
| 2015/0366176 A1* | 12/2015 | Fenchak | C05F 17/0009 |
| | | | 119/6.7 |

FOREIGN PATENT DOCUMENTS

| | | |
|---|---|---|
| CN | 102574746 | 7/2012 |
| EP | 0196887 A2 | 10/1986 |
| EP | 2100866 A2 | 9/2009 |
| FR | 3000062 | 6/2014 |
| IN | 1579CHE2011 | 9/2011 |
| WO | 9310060 A1 | 5/1993 |

* cited by examiner

WORM HARVESTING APPARATUS

FIELD OF THE INVENTION

The present invention relates to the field of worm harvesting. More particularly, the invention relates to worm harvesting apparatus for optimizing the breeding and growth of worms from organic waste introduced thereto.

BACKGROUND OF THE INVENTION

Many devices have been employed for utilizing earthworms to convert organic waste to environmentally compatible products, such as vermicompost. Some devices are used for household waste and some are used for converting large commercial volumes of organic waste, including agriculture, sludge and municipal waste.

US 2003/0059931, for example, discloses a composting apparatus that includes a housing and a plurality of composting drawers in a stacked relationship within the housing. Compostable material and composting organisms are received within each drawer, and the bottom region of each drawer has a plurality of apertures sized to permit the composted material to pass therethrough. A plurality of receiving structures within the housing are respectively disposed under the drawers to receive the composted material. After the macro-organisms migrate toward the top of each drawer to access and process fresh compostable material and the bottom layer of the composted material is removed, all material including the macro-organisms in the drawer moves downward for reuse.

EP 0196887 discloses a composting plant comprises a cruciform-type breaker bar unit for moving the bottom layer of worm processed compost through the perforated floor of the plant.

IN 1579CHE2011 discloses a vermicomposting system that comprises a plurality of parallel stacks arranged between a loading module and an unloading module, and a plurality of vermicomposting modules mounted in each stack. The stack is inclined downwardly towards the unloading module. The slope of the stack is based on the desired rate of free movement of the vermicomposting modules under gravity along the stack from the loading module end to the unloading module end.

The devices of the aforementioned publications are intended to generate compost and not to harvest worms, particularly since the discharged compost is substantially worm free and most of the worms are retained in the remaining biomass which is not climate controlled.

It is an object of the present invention to provide worm harvesting apparatus for optimizing growth of worms from organic waste introduced thereto.

It is an additional object of the present invention to provide worm harvesting apparatus for facilitating removal of fully grown worms as well as worm processed byproducts.

It is an additional object of the present invention to provide worm harvesting apparatus that significantly reduces the amount of manual labor that is needed to harvest worms, relative to prior art apparatus.

Other objects and advantages of the invention will become apparent as the description proceeds.

SUMMARY OF THE INVENTION

The present invention provides a worm harvesting system, comprising (a) a vermiculture unit, comprising structural elements that define a hollow interior fillable with an introducible organic substance and through which worms for converting said organic substance to environmentally compatible products are able to migrate; a perforated surface for supporting said organic substance; solid and fixed walls of said structural elements extending upwardly from said perforated surface to a void area located below an uppermost edge of said structural elements, removal of worms from a region of said interior that is below said void area being prevented by said solid and fixed walls; and (b) an extractor insertable into said interior via said void area, for extracting, from said hollow interior, solidified organic substance to which the worms have upwardly migrated, allowing grown worms to be separated from said extracted organic substance and collected.

In one aspect, the extractor is a single extendable openwork drawer member positioned above said perforated surface and at an uppermost layer of said interior, and in movable engagement with one of said structural elements, wherein a rear wall of said drawer member is configured, when extended, to displace outwardly from said hollow interior solidified organic substance to which the worms have upwardly migrated, allowing grown worms to be separated from said displaced organic substance and collected.

In one aspect, the structural elements define a service tunnel below the drawer member through which the worms are able to migrate from the perforated surface into the drawer member. Environment control elements may be mounted to one or more walls of the service tunnel for generating a worm-beneficial temperature and moisture level within a service tunnel interior.

In one aspect, the worm harvesting system further comprises an inclined surface for receiving downwardly discharged worm processed byproducts.

In one aspect, the openwork drawer member is topless and bottomless.

In one aspect, the openwork drawer member is perforated.

In one aspect, the worm harvesting system further comprises a sorting device for receiving the organic substance extracted from the drawer member, for filtering the worms from the extracted organic substance, and for sorting the filtered worms into several defined sizes.

In one aspect, the worm harvesting system further comprises a collecting receptacle for receiving the worm processed byproducts from the bottom of the inclined surface.

In one aspect, the worm harvesting system comprises a plurality of the vermiculture units that are arranged such that they are concatenated, in order to maximize utilization of floor area. The solid and fixed walls may be front and rear walls.

The present invention is also directed to vermicomposting apparatus, comprising structural elements that define a hollow interior fillable with an introducible organic substance and through which worms for converting said organic substance to environmentally compatible products are able to migrate; a perforated surface for supporting said organic substance; and an inclined surface for receiving worm processed byproducts downwardly discharged through said perforated surface.

DETAILED DESCRIPTION OF PREFERRED EMBODIMENTS

The present invention is worm harvesting apparatus for harvesting worms by converting an organic substance, including animal manure and organic municipality solid waste such as household waste, into protein through worm processing. The harvested worms, composed mainly of protein, are discharged after having decomposing the organic substance and increasing in size, in order to be fed to living creatures, such as fish and poultry.

The apparatus comprises one or more vermiculture units fillable with an organic substance and through which the worms are able to migrate. The organic substance introduced into a vermiculture unit is generally pretreated by a bacterial biological action which causes it to be heated to an initial temperature of approximately 50° C., while being oxygenated and mixed. This pretreated substance is introduced into a vermiculture unit. If so desired, the pretreatment may take place within the vermiculture unit.

Each vermiculture unit is configured with an open top and one or more perforated horizontal surfaces, and comprises an extendable drawer member positioned at an upper layer of the unit for discharging organic substance containing the grown worms, a service tunnel below the drawer member, a soil-breaker-bar system operatively connected to the lower perforated surface, and an inclined surface below the perforated floor surface. The structure of the apparatus facilitates concatenation of units, placed one on top of the other, or in a side-by-side arrangement, in order to maximize utilization of floor area. Ventilation and heating elements are mountable within the service tunnel in order to control the climate conditions to which the worms are exposed.

The apparatus is based on a vertical feed arrangement by which an organic substance is introduced at the top of a vermiculture unit and worm excretions such as bio-humus are discharged at its bottom through the lower perforated floor surface.

Figure 1:
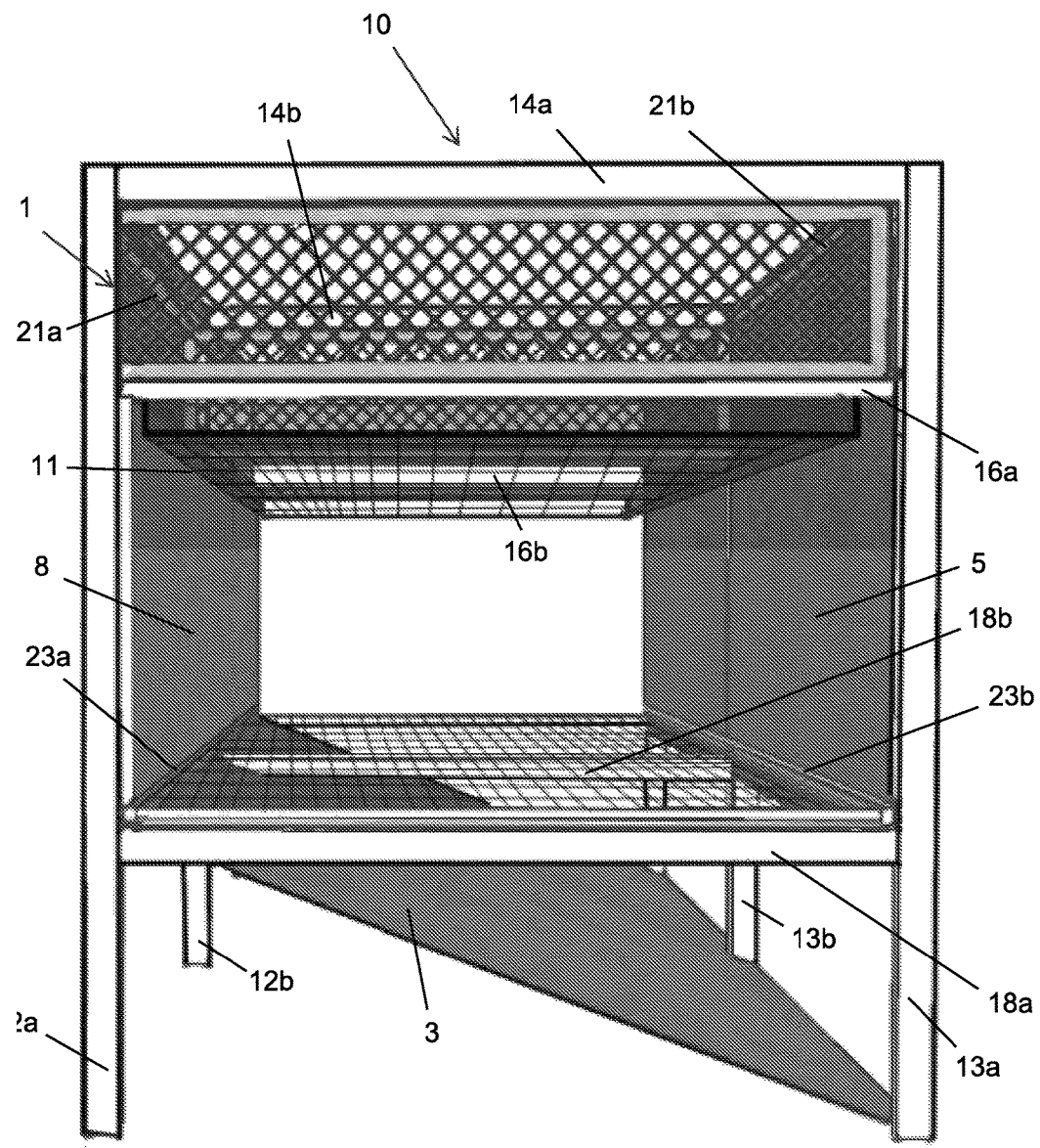
FIG. 1 is a perspective view from the side of an unfilled vermiculture unit, according to one embodiment of the present invention.

FIG. 1 illustrates a vermiculture unit, generally indicated by numeral 10, according to one embodiment of the present invention. Vermiculture unit 10 is shown to assume a rectilinear configuration to facilitate concatenation as will be described hereinafter, but it will be appreciated that any other configuration is also within the scope of the invention.

The structural elements of vermiculture unit 10 defining a frame include vertically extending and longitudinally spaced posts 12a-b and 13a-b, transversally extending and longitudinally spaced upper cross members 14a-b, drawer supports 16a-b, lower perforated surface supports 18a-b, and longitudinally extending and transversally spaced upper members 21a-b, lower members 23a-b, and drawer frame member 11. The structural elements are made of any good load bearing material such as metal and plastic, and generally have a uniform cross section.

As referred to herein, "longitudinal" means along the length of the vermiculture unit and "transversal" means along the width of the vermiculture unit.

A rear wall 5, e.g. a wooden wall, is secured to posts 13a and 13b and to members 21b and 23b. A front wall 8, e.g. a wooden wall, of a lower height than rear wall 5 is secured to posts 12a and 12b and to members 11 and 23a. Extending downwardly from member 23a to the bottom of posts 13a and 13b is inclined surface 3, which is configured by a suitable inclination to ensure movement of bio-humus therealong gravitationally to its bottom for collection.

A single drawer member 1 is fitted between upper cross members 14a-b and drawer supports 16a-b.

Figure 2:
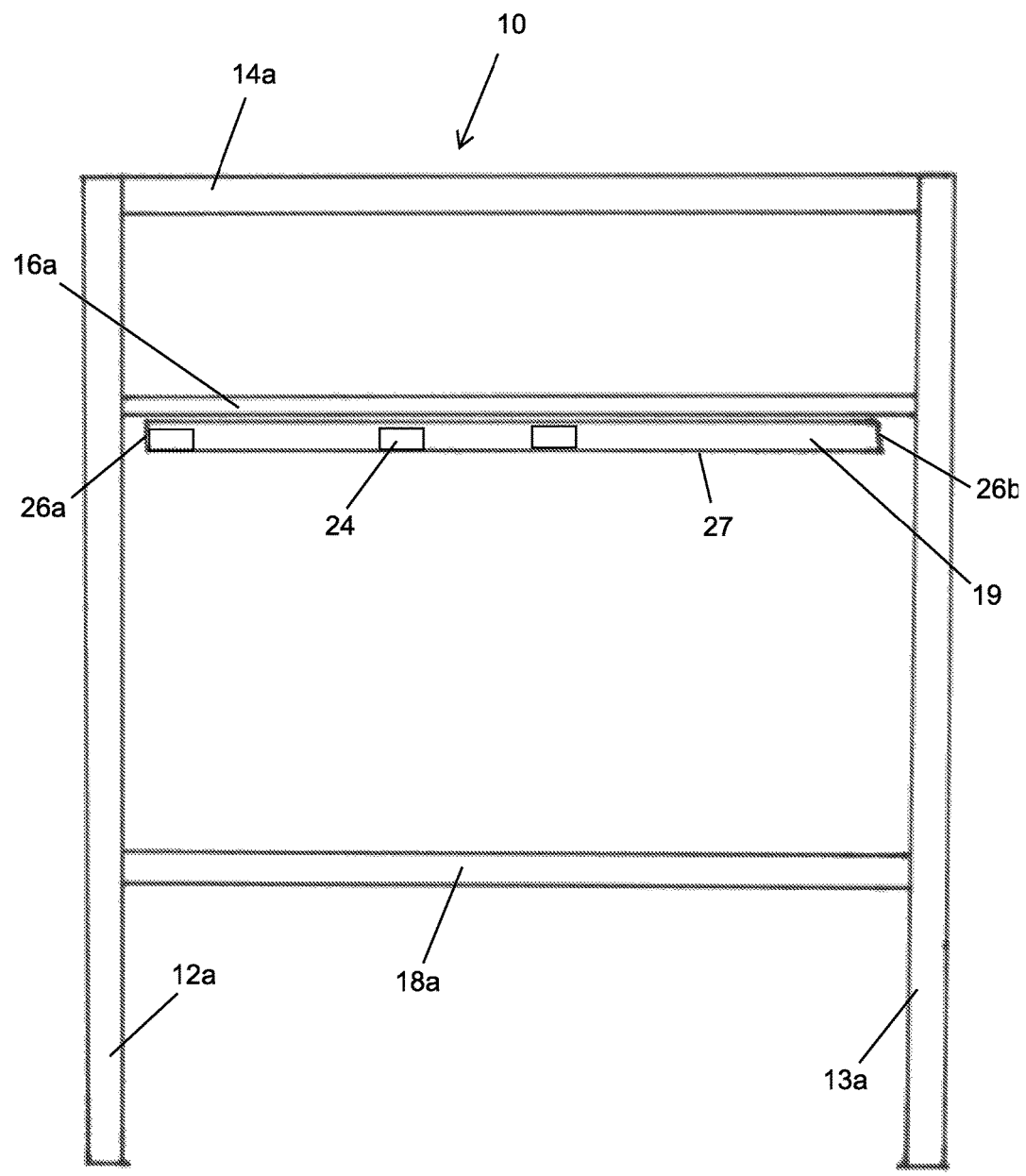
FIG. 2 is a side view of the vermiculture unit of FIG. 1, schematically illustrating climate control elements that are attached to the service tunnel.

As shown in FIG. 2, a hollow, small-volume service tunnel 19 is provided in abutting relation with, and below, drawer supports 16a-b of vermiculture unit 10. The schematically illustrated climate control elements 24 for maintaining a worm-beneficial temperature and/or a worm-beneficial moisture level that are often significantly different than the climatic conditions externally to vermiculture unit 10 are attachable to the walls of service tunnel 19. Climate control elements 24, which may be self-regulating, may include, but are not limited to, heating elements, aeration elements, ventilation elements, and moisture control elements. The walls of service tunnel 19 are preferably perforated, including horizontal surface 27, to allow the service tunnel to be in fluid communication with the remaining interior of vermiculture unit 10 and to enable passage of worms therethrough. The height of service tunnel 19 may range from 2-5 cm. The transversal ends 26a and 26b of service tunnel 19 may be transversally spaced from posts 12a and 13a, respectively.

Figure 3:
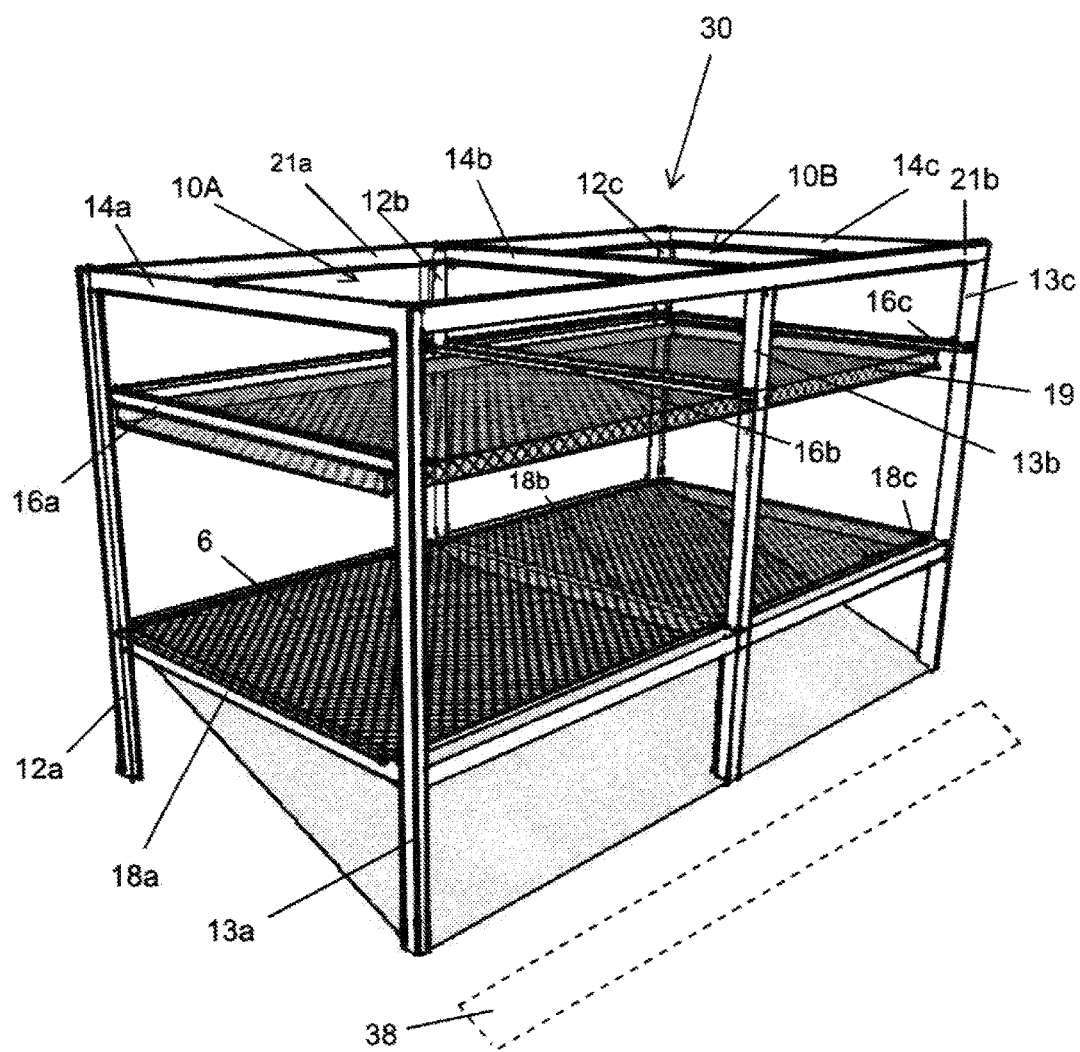
FIG. 3 is a perspective view from the rear of worm harvesting apparatus that includes two vermiculture units of FIG. 1, showing upper and lower perforated surfaces.

FIG. 3 illustrates worm harvesting apparatus 30 that includes two vermiculture units 10A-B, with the addition of posts 12c and 13c and transversally extending members 14c, 16c and 18c. Posts 12b and 13b, upper cross member 14b, and lower perforated surface support 18b are common to the two vermiculture units 10A-B, for efficient space utilization. Upper members 21a-b, as well as service tunnel 19 which is shown to be perforated, and lower perforated surface 6, longitudinally extend throughout the entire length of apparatus 30. While service tunnel 19 underlies members 16a-c, lower perforated surface 6 overlies members 18a-c, although any other arrangement with respect to the cross members may also be possible.

Figure 4:
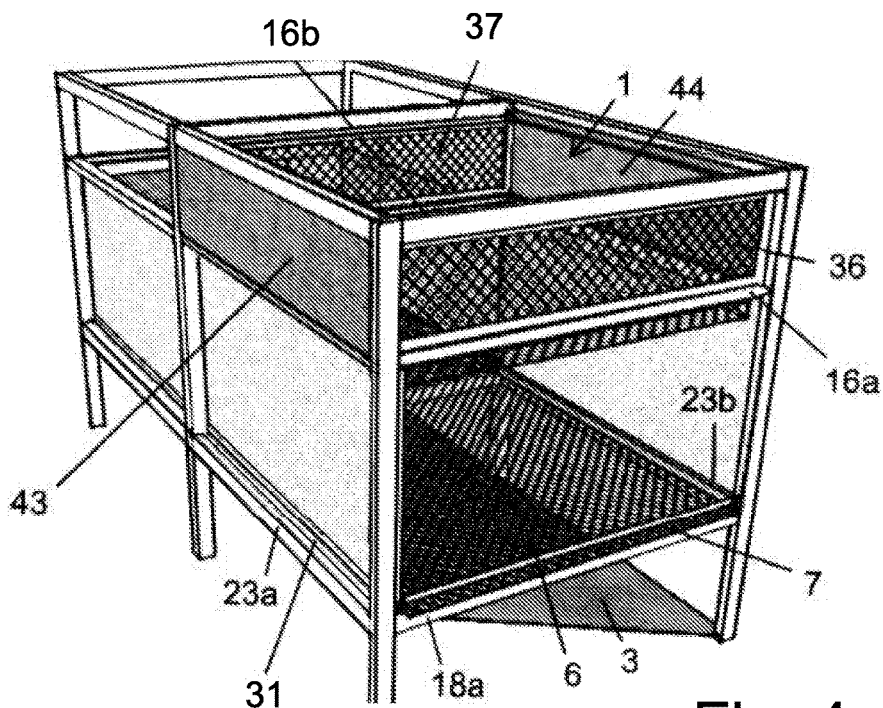
FIG. 4 is a perspective view from the front of the worm harvesting apparatus of FIG. 3, showing the drawer member in a closed position.

As shown in FIG. 4, soil-breaker bar 7 is operatively and movably connected to lower members 23a-b, allowing bar 7 to be displaced from support 18a to 18c and to thereby cause organic mass located on top of lower perforated surface 6 to become granulated or disintegrated upon being contacted by the moving bar. The combination of lower perforated surface 6 and soil-breaker bar 7 constitutes a castings discharge system. The castings, which are generally bio-humus, are discharged through the perforations of surface 6 and fall on inclined surface 3.

A longitudinally extending rod 31 or any other type of track protrudes upwardly from each of lower members 23a-b and is engaged with a corresponding end of soil-breaker bar 7 by any means well known to those skilled in the art, such as a displaceable toothed connection, and may be driven by a motor and winch.

Figure 5:
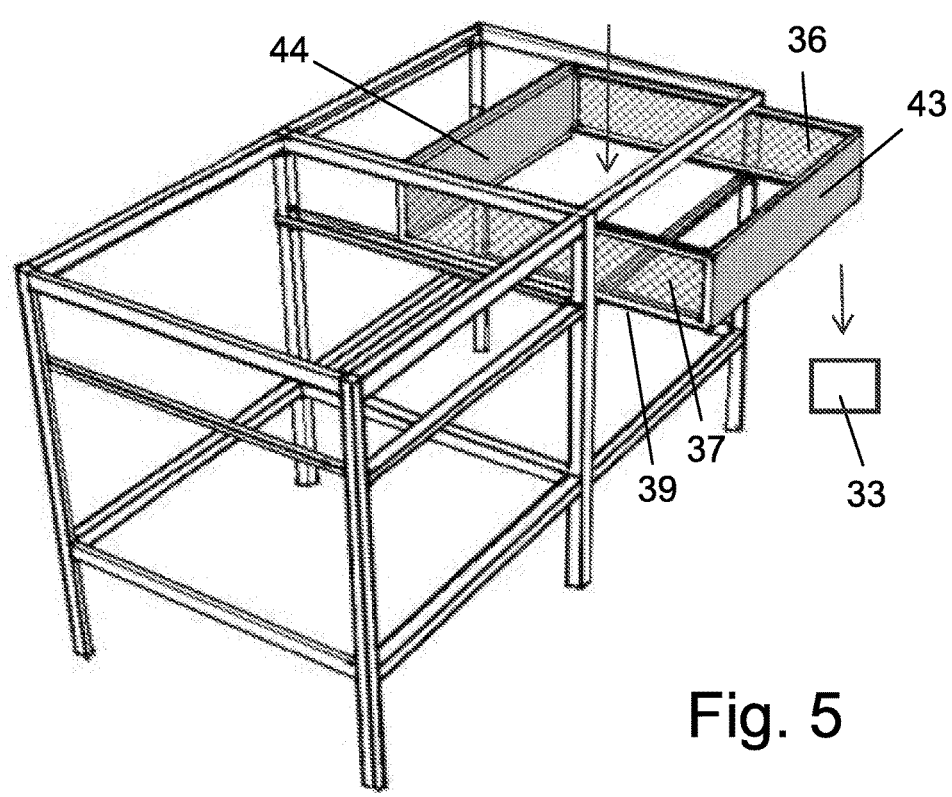
FIG. 5 is a perspective view from the front and top of the structural elements of the worm harvesting apparatus of FIG. 3, showing the drawer member in a retracted position.

Drawer member 1 is shown to be at a dosed or retracted position in FIG. 4, and at an extended position in FIG. 5. Drawer member 1, which is located at an uppermost region of the apparatus, comprises perforated side walls 36 and 37 that have a corresponding bottom edge 39 that is slidably engageable with drawer supports 16a-b, respectively, for example in cooperation with a slide mechanism. Imperforated front wall 43 and rear wall 44 are connected to side walls 36 and 37, defining a topless and bottomless drawer member to permit the passage of organic waste and worms therethrough. The height of drawer member 1 may range from 5-50 cm, e.g. 30 cm.

The height of the vermiculture unit is dependent upon the type or species of worm being harvested and upon its development time and life cycle.

In use, lower perforated surface 6 is first covered by a relatively rigid, biodegradable barrier such as cardboard for retaining worms that have been seeded into the interior of the apparatus by use of a worm seeding substrate and for preventing them from falling through the perforations. Many different species of worms are suitable to be harvested within the apparatus, including Red Wigglers (*Eisenia fetida*) and tropical earthworm species.

An organic substance serving as food for the worms, separately or together with bedding material, is then introduced into the interior of the vermiculture unit, to generate vermicompost. An additional small layer of organic substance is introduced each week, so that after approximately 3 months the entire interior becomes filled. The biodegradable barrier becomes disintegrated when vermicompost has sufficiently accumulated and has become rigid. During this period of time, it is not necessary to remove castings and the biodegradable materials, which have begun to decompose and be discharged through the lower perforated surface onto the inclined surface.

Although any suitable compostable material may be introduced into the apparatus, the preferred compostable material for producing protein particularly and not just compost is organic waste in a state of decomposition including, but is not limited to, consumer food waste, agricultural waste such as manure and crop residuals, municipal organic solid waste, and industrial organic sludge. All of the aforementioned types of organic waste are preferably pre-treated so as to be eatable by the worms.

The worms consume the organic substance and migrate upwardly in quest of new substance, after lower layers have been exhausted. They are able to enter the interior of drawer member 1 through the horizontal perforated surface 27 of service tunnel 19. During their upward path, the worms generate layers of vermicompost and cocoons, i.e. worm eggs. In addition to the upward migration, the worms are able to migrate longitudinally within the interior of the apparatus, such as through the service tunnel, from one vermiculture unit to another. As a result of this biological process, most of the worms will be found in the current uppermost waste layer. After a sufficient period of time has elapsed, the cocoons will hatch and the newly hatched worms will also migrate upwardly in quest of organic substance, joining the adult worms that are already found in the uppermost layer.

The worms that have migrated upwardly may be harvested at regular intervals of time or when the density of worms within the interior of drawer member 1 is greater than a predetermined value In order to harvest the worms, the bottomless drawer member is extended from the frame of the apparatus. Extension of drawer member 1 causes its rear wall 44 to outwardly displace the uppermost layer of organic substance contacted thereby. Since the outwardly displaced organic substance provided with a high density of worms is unsupported from below, the organic substance falls into a collection member 33. Collection member 33 may be a sorting device for filtering the worms from the organic substance and for sorting worms into several defined sizes. Drawer member 1 is then inwardly displaced to its original position with respect to the frame, and the filtered organic substance is returned to the interior of the drawer member. A partial quantity of the sorted worms may be returned to drawer member 1, to digest newly introduced organic substance and to provide a basis for future breeding.

The worms that have been filtered are sent to an external processing facility, whereat they are dried and then disintegrated. The disintegrated worm matter containing large amounts of protein is fed to living creatures, such as fish and poultry.

Alternatively, the worms that have migrated upwardly may be harvested by means of an extractor adapted to selectively remove at least a portion of organic substance, preferably solidified, to which the worms have upwardly migrated. By virtue of the configuration of the vermiculture unit by which the lower solid and fixed walls prevent extraction of organic substance, the extractor is insertable into the vermiculture interior via a void area only above the solid and fixed walls. The extractor may be a hand held implement such as one having a planar extracting surface for forcibly displacing outwardly a layer of the organic substance provided with a high density of worms, or one with a concavity for receiving a portion of the uppermost layer of organic substance. The extractor may also be mechanized or motorized, to enable remote or automatic operation of the extraction process.

The single drawer member 1 located at the uppermost organic waste layer serves to maximize discharge of fully developed worms, for the subsequent disintegration thereof into high protein pieces to be fed to living creatures being bred, such as fish and birds. As the vermiculture unit has solid and fixed front and rear walls, worms are unable to be removed from the layers of organic mass underlying drawer member 1 and are urged to pass through service tunnel 19. Service tunnel 19 accordingly functions as a volume within which worms are able to be optimally grown, particularly due to the operation of the environment control elements fixated to one or more of its walls for maintaining a substantially uniform worm-beneficial temperature of approximately 25° C. and a substantially uniform worm-beneficial moisture level within the service tunnel interior. The worm-beneficial temperature and worm-beneficial moisture level are generally unique for the given worm being harvested. For example, *Eisenia fetida* worms are at a risk of death at temperatures below 10° C. and above 35° C., and a suitable temperature range for optimal worm productivity is 15-25° C., while the suitable temperature range for tropical earthworms is 15-40° C.

Castings are able to be removed through the lower perforated surface after worms have reached the uppermost waste layer, the migration time to the uppermost layer corresponding to the hatching time of cocoons located in the lower layers and the development time of the hatched cocoons until they develop to mature worms to ensure that the cocoons will not be discharged from the lower perforated surface. After a portion of the vermicompost has been removed, the overlying mass descends gravitationally, vacating some of the apparatus volume to allow additional fresh food or other organic matter to be introduced through the interior of the drawer device. Castings and bio-humus may be removed at regular intervals through the use of the soil-breaker bar, depending on environmental conditions, the given worm species, and the type of organic substance that has been introduced.

The castings and bio-humus that are discharged through the lower perforated surface fall on the inclined surface, and are thereby caused to be displaced outwardly from the apparatus, gravitationally or by a mechanical element that may function as a wiper. The single inclined surface that longitudinally extends throughout the entire length of the apparatus efficiently utilizes the floor space underlying the apparatus. The discharge may be collected into a central collecting receptacle 38 (FIG. 3).

It will be appreciated that the configuration of the inclined surface and or the service tunnel may be implemented with respect to vermicomposting apparatus.

Figure 6:
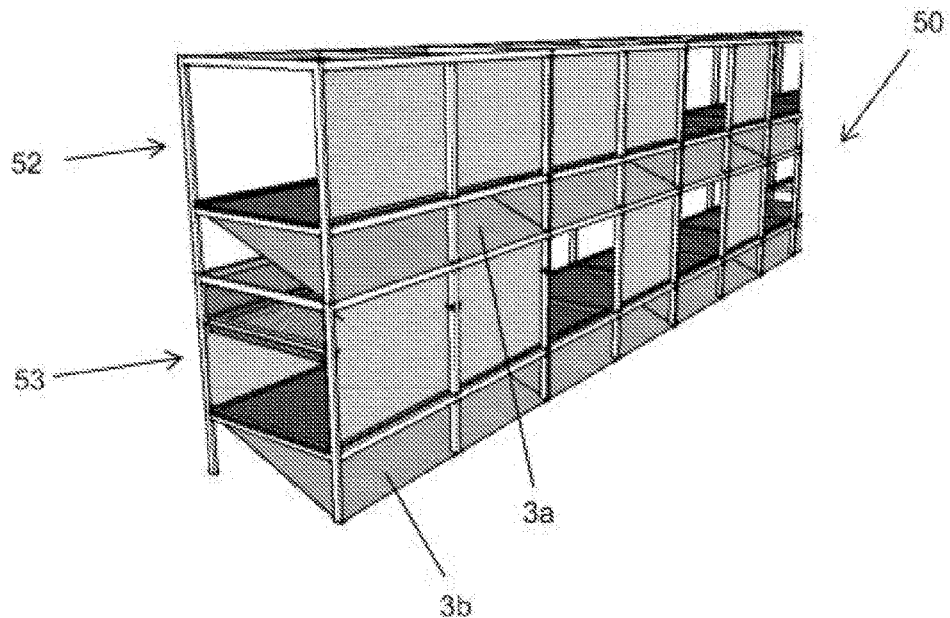
FIG. 6 is a perspective view from the rear of worm harvesting apparatus that includes a plurality of concatenated vermiculture units of FIG. 1.
Figure 7:
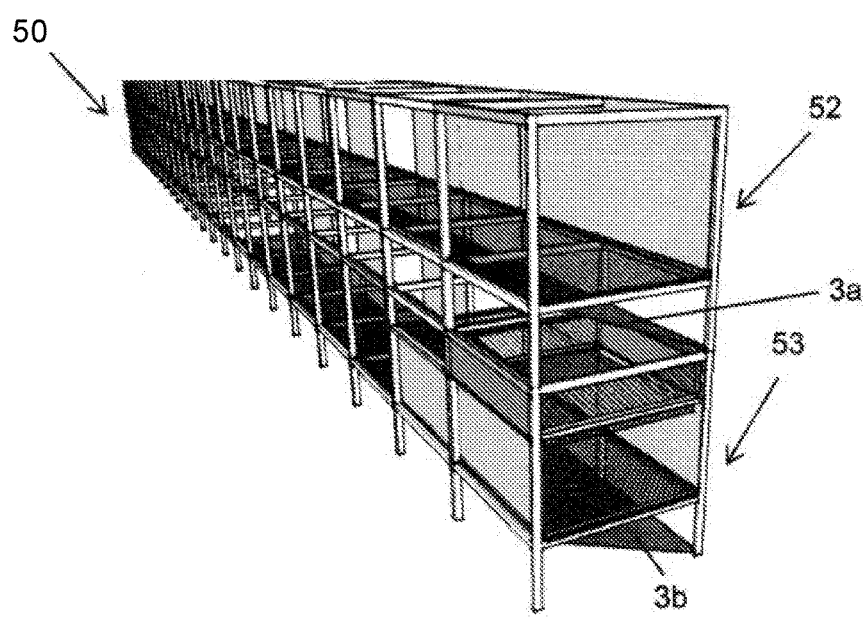
FIG. 7 is a perspective view from the front of the worm harvesting apparatus of FIG. 6.

FIGS. 6 and 7 illustrate another embodiment of the invention wherein apparatus 50 comprises two rows 52 and 53 of vermiculture units that are stacked one on top of the other in aligned fashion. The upper cross members of the lower row 53 serve as the lower perforated surface supports of the upper row 52, to conserve space. If desired, more than two rows may be employed. Each row comprises a plurality of contiguous units, for example 20 units. The discharge from row 52 is delivered from common inclined surface 3a, and the discharge from row 53 is delivered from common inclined surface 3b, to the central collecting receptacle. Each common inclined surface may be comprised of a plurality of contiguous plates. The proximity of contiguous vermiculture units, both longitudinally and vertically, also increases the amount of worms that can be harvested for a given surface area.

Such apparatus comprising a large number of concatenated vermiculture units supports an economically viable commercial process for processing a large volume of organic waste and thereby breeding and harvesting a correspondingly large volume of earthworms. The worms are able to be constantly bred throughout the year and during all-weather conditions by virtue of the heating and ventilation elements that are provided within the perforated service tunnel for maintaining optimal growth conditions, such as by controlling the temperature and humidity of the substrate in which the worms grow in size. In addition, the worms' digestion system produces a humus based compost as a byproduct, for increased revenue. The compost, which is a self-adhered layer of castings, falls onto the inclined surface after being granulated and is collected from all vermiculture units and from each level, into the central collecting receptacle by a substantially continuous process. This substantially continuous process, by which organic waste is introduced and fully grown worms and compost are discharged, significantly reduces the amount of manual labor that is required in comparison to prior art apparatus.

While some embodiments of the invention have been described by way of illustration, it will be apparent that the invention can be carried out with many modifications, variations and adaptations, and with the use of numerous equivalents or alternative solutions that are within the scope of persons skilled in the art, without exceeding the scope of the claims.

The invention claimed is:
1. A worm harvesting system, comprising:
a) a vermiculture unit, comprising:
 i. structural elements that define a hollow interior fillable with an introducible organic substance and through which worms for converting said organic substance to environmentally compatible products are able to migrate;
 ii. a perforated surface for supporting said organic substance; and
 iii. solid and fixed walls of said structural elements extending upwardly from said perforated surface to a void area located below an uppermost edge of said structural elements, removal of worms from a region of said interior that is below said void area being prevented by said solid and fixed walls; and
b) an extractor insertable into said interior via said void area, for extracting, from said hollow interior, solidified organic substance to which the worms have upwardly migrated, allowing grown worms to be separated from said extracted organic substance and collected.

2. The worm harvesting system according to claim 1, wherein the extractor is a single extendable openwork drawer member positioned above the solid and fixed walls and at an uppermost layer of the interior, and in movable engagement with one of the structural elements, wherein a rear wall of said drawer member is configured, when extended, to displace outwardly from the hollow interior the solidified organic substance to which the worms have upwardly migrated.

3. The worm harvesting system according to claim 2, wherein the structural elements define a service tunnel below the drawer member through which the worms are able to migrate from the perforated surface into the drawer member.

4. The worm harvesting system according to claim 3, further comprising environment control elements mounted to one or more walls of the service tunnel for generating a worm-beneficial temperature and moisture level within a service tunnel interior.

5. The worm harvesting system according to claim 4, wherein the environment control elements are selected from the group consisting of heating elements, aeration elements, ventilation elements, moisture control elements, and self-regulating environment control elements.

6. The worm harvesting system according to claim 2, wherein the openwork drawer member is topless and bottomless.

7. The worm harvesting system according to claim 2, wherein the openwork drawer member is perforated.

8. The worm harvesting system according to claim 1, further comprising an inclined surface for receiving downwardly discharged worm processed byproducts.

9. The worm harvesting system according to claim 8, further comprising a collecting receptacle for receiving the worm processed byproducts from the bottom of the inclined surface.

10. The worm harvesting system according to claim 8, wherein the structural elements comprise:
a) vertically extending first, second, third and fourth posts, wherein said second post is longitudinally spaced from said first post and said fourth post is longitudinally spaced from said third post, and said first and third posts are transversally aligned and said second and fourth posts are transversally aligned;
b) a first upper cross member transversally extending between an upper end of said first and third posts, and a second upper cross member transversally extending between an upper end of said second and fourth posts;
c) a first upper member longitudinally extending between an upper end of said first and second posts, and a second upper member longitudinally extending between an upper end of said third and fourth posts;

d) a first perforated surface support transversally extending between said first and third posts, and a second perforated surface support transversally extending between said second and fourth posts;

e) a first lower member longitudinally extending between said first and second posts and connected to said first and second perforated surface supports, and a second lower member longitudinally extending between said third and fourth posts and connected to said first and second perforated surface supports;

f) a first drawer support transversally extending between said first and third posts and intermediate to said first upper cross member and said first perforated surface support, and a second drawer support transversally extending between said second and fourth posts and intermediate to said second upper cross member and said second perforated surface support; and g) a first drawer frame member longitudinally extending between said first and second posts and connected to said first and second drawer supports, and a second drawer frame member longitudinally extending between said third and fourth posts and connected to said first and second drawer supports.

11. The worm harvesting system according to claim 10, wherein a rear wall is secured to the third and fourth posts and to the second upper member and the second lower member, and a front wall of a lower height than said rear wall is secured to the first and second posts and to the first drawer frame member and the first lower member.

12. The worm harvesting system according to claim 11, wherein the inclined surface extends downwardly from the first lower member to a lower portion of the third and fourth posts.

13. The worm harvesting system according to claim 10, wherein the drawer member is movably fitted between the first and second upper cross members and between the first and second drawer supports.

14. The worm harvesting system according to claim 1, further comprising a sorting device for receiving the extracted organic substance, for filtering the worms from the extracted organic substance, and for sorting the filtered worms into several defined sizes.

15. The worm harvesting system according to claim 1, comprising a plurality of the vermiculture units, wherein said plurality of vermiculture units are concatenated.

16. The worm harvesting system according to claim 15, wherein the concatenated units are positioned one on top of the other or in a side-by-side arrangement.

17. The worm harvesting system according to claim 16, wherein the concatenated units are positioned one on top of the other and in a side-by-side arrangement.

18. The worm harvesting system according to claim 17, wherein the solid and fixed walls are front and rear walls.

19. Vermicomposting apparatus, comprising:
a) structural elements that define a hollow interior fillable with an introducible organic substance and through which worms for converting said organic substance to environmentally compatible products are able to migrate;
b) a perforated surface for supporting said organic substance;
c) an inclined surface for receiving worm processed byproducts downwardly discharged through said perforated surface; and
d) a service tunnel above the perforated surface to which the worms are able to migrate, for generating a worm-beneficial temperature and moisture level within a service tunnel interior.

* * * * *